United States Patent [19]

Shimizu et al.

[11] 4,254,292

[45] Mar. 3, 1981

[54] METHOD FOR PREPARING POLYCYCLIC AROMATIC HYDROCARBONS

[75] Inventors: Isoo Shimizu; Okitsugu Tsuji, both of Yokohama; Eiichi Matsuzaka; Atsushi Sato, both of Tokyo, all of Japan

[73] Assignee: Nippon Petrochemicals Co., Ltd., Tokyo, Japan

[21] Appl. No.: 85,979

[22] Filed: Oct. 18, 1979

[30] Foreign Application Priority Data

Oct. 25, 1978 [JP] Japan ................. 53-131205

[51] Int. Cl.$^3$ .................. C07C 2/20; C07C 15/12
[52] U.S. Cl. .................. 585/320; 585/406; 585/422; 585/428
[58] Field of Search ............. 585/320, 406, 422, 428

[56] References Cited

U.S. PATENT DOCUMENTS

| | | | |
|---|---|---|---|
| 2,249,987 | 7/1941 | Stanley et al. | 585/406 |
| 2,519,577 | 8/1950 | Ipatieff et al. | 585/406 |
| 3,272,879 | 9/1966 | Stahly | 585/320 |

FOREIGN PATENT DOCUMENTS

| | | |
|---|---|---|
| 48-44240 | 6/1973 | Japan . |
| 52-148053 | 12/1977 | Japan . |
| 896864 | 5/1962 | United Kingdom . |
| 959355 | 6/1964 | United Kingdom . |
| 977322 | 12/1964 | United Kingdom . |
| 1530430 | 11/1978 | United Kingdom . |

*Primary Examiner*—Veronica O'Keefe
*Attorney, Agent, or Firm*—Fisher, Christen & Sabol

[57] ABSTRACT

A method for preparing polycyclic aromatic hydrocarbons with excellent yield and selectivity but without the formation of cyclic dimers and other undesirable by-products. In the method of the present invention, styrene, α-methylstyrene, β-methylstyrene and/or vinyltoluene is dimerized and/or codimerized to produce unsaturated dimer and/or codimer in the first step reaction and said unsaturated dimer and/or codimer is caused to react with an aromatic hydrocarbon or hydrocarbons in the second step reaction, and both the first and second step reactions are carried out in the presence of a catalyst which is represented by the general formula: $RCF_2SO_3H$, in which the symbol R is Cl, F or $C_nF_pCL_{2n+1-p}$, wherein n is an integer from 1 to 3 and p is also an integer from 1 to $2n+1$.

7 Claims, No Drawings

4,254,292

METHOD FOR PREPARING POLYCYCLIC AROMATIC HYDROCARBONS

BACKGROUND OF THE INVENTION

1. Field of the Invention

This invention relates to a method for preparing polycyclic aromatic hydrocarbons. More particularly, the invention relates to an improved method for preparing polycyclic aromatic hydrocarbons from an aromatic hydrocarbon and two molecules of styrene in good yield.

2. Description of Prior Art

The distyrenated aromatic hydrocarbon, that is, one of polycyclic aromatic hydrocarbons, is prepared by aralkylating an aromatic hydrocarbon molecule with two molecules of styrene. The distyrenated aromatic hydrocarbon is quite excellent in compatibility and thermal stability, and the compound itself is effectively used as a plasticizer, a lubricant, an electrical insulating oil and so forth. In addition, by hydrogenerating the distyrenated aromatic hydrocarbon, it is employed as a high-energy fuel and a lubricating oil. Therefore, the distyrenated aromatic hydrocarbon is one of the important industrial raw materials.

In connection with the method for preparing the distyrenated aromatic hydrocarbons by aralkylating aromatic hydrocarbons with styrenes, there have been proposed several methods in, for example, British Pat. No. 896,864, No. 959,355 and No. 977,322, in which methods, alkylbenzenes are aralkylated with styrenes by using concentrated sulfuric acid or a solid acid such as acid clay. In all of these conventional methods, both the monostyrenated product and the distyrenated product are simultaneously formed, and therefore, these methods are not serviceable for the preparation of the sole distyrenated product.

BRIEF SUMMARY OF THE INVENTION

The inventors of the present application have found out a novel catalyst with which the polycyclic atomatic hydrocarbons such as distyrenated aromatic hydrocarbons can be produced by carrying out the reaction in two steps, thereby accomplishing the present invention.

It is, therefore, the primary object of the present invention to provide a novel method for preparing polycyclic aromatic hydrocarbons.

Another object of the present invention is to provide a method for preparing polycyclic aromatic hydrocarbons which is free from the above-mentioned disadvantages in the conventional art.

A further object of the present invention is to provide a method for preparing polycyclic aromatic hydrocarbons which can be performed without difficulty in industrial scale.

In accordance with the present invention, the preparation of the polycyclic aromatic hydrocarbons is carried out through two steps of reactions in the presence of a catalyst which is represented by the general formula: $RCF_2SO_3H$, that is, in the first step, at least one compound selected from the group consisting of styrene, α-methylstyrene, β-methylstyrene and vinyltoluene is dimerized and/or codimerized to produce an unsaturated dimer and/or condimer, and in the second step, the above unsaturated dimer and/or codimer is subjected to react with an aromatic hydrocarbon. In the above catalyst, $RCF_2SO_3H$, the symbol R represents chlorine atom (Cl), fluorine atom (F) or a radical represented by the general formula: $C_nF_pCl_{2n=1-p}$, wherein n is an integer from 1 to 3, inclusive and p is also an integer from 1 to 2n+1, inclusive.

DETAILED DESCRIPTION OF THE INVENTION

As described above, the reaction of the present invention is carried out in two steps. That is, in the reaction of the first step, the unsaturated dimers and/or codimers of styrenes are produced by selective dimerization and/or codimerization of styrenes. Then, the aromatic hydrocarbons are aralkylated with the above unsaturated dimers and/or codimers in the reaction of the second step.

The specific catalyst that is used for the above-mentioned two step reactions has both the activity to the selective formation of unsaturated dimers of styrenes and the activity to the aralkylation. Therefore, even though the reaction is carried out in two steps, it is not necessary to remove the catalyst and to separate and refine the unsaturated dimers and/or codimers after the first step reaction and it is possible to perform the second step reaction of aralkylation in succession to the first step reaction. In addition to that, the reaction conditions for the second step reaction (aralkylation) can be made the same as those of the first step reaction (unsaturated dimerization). In the present invention, since the expensive reaction materials of styrenes can be selectively converted into the aimed polycyclic aromatic hydrocarbons such as distyrenated aromatic hydrocarbon, the advantage of the present invention in industrial viewpoint is quite large.

The conventional methods for producing unsaturated dimers which correspond to the reaction products of the first step in the method of the present invention have been proposed in, for example, Japanese Published Unexamined Patent Application No. Sho. 48-44240 (1973) and No. Sho. 52-148053 (1977). In these methods, styrenes are dimerized in the presence of the catalyst such as solid acid, cation exchange resin or clay, while, in order to suppress the cyclic dimerization of styrenes, the dimerization is performed under the coexistence of a cyclic dimerization inhibitor such as aldehyde, ketone or alcohol. However, the second step aralkylation cannot be carried out under the coexistence of the cyclic dimerization inhibitor. Furthermore, when the obtained unsaturated dimer is refined by removing the catalyst and the above cyclic dimerization inhibitor, and an aromatic compound is aralkylated in the presence of sulfuric acid or a solid actic catalyst that is proposed as the catalyst for adding styrene to aromatic hydrocarbons, the cyclization of the unsaturated dimer is caused to occur. Therefore, the formation of the cyclic dimer by-product cannot be avoided and the aimed polycyclic aromatic hydrocarbon cannot be obtained selectively. Accordingly, even by employing the combination of the conventional methods, it is impossible to prepare selectively the objective polycyclic aromatic hydrocarbons.

In the method of the present invention, styrenes used as the raw materials for the first step reaction include styrene itself, α-methylstyrene, β-methylstyrene and vinyltoluene. These materials may be used solely to form an unsaturated dimer or used in combination of two or more kinds to form unsaturated codimers. These reaction products are used for the aralkylation of the second step reaction.

The aromatic hydrocarbons which are used as the raw materials for the second step reaction are saturated aromatic hydrocarbons which include polycyclic aromatic compounds such as naphthalenes, biphenyls and diphenyl alkanes as well as the monocyclic aromatic compounds such as benzene, alkylbenzenes and tetralines. In the case that the aromatic compound has side chain alkyl groups, the aromatic compound may have at least one carbon atom to be aralkylated in the aromatic ring or rings. The aromatic compound can be used irrespectively of the kinds of alkyl groups such as branched chain alkyl groups and straight chain alkyl groups, and the number of alkyl groups. It is preferable, however, that the positions of the side chains of the aromatic compound may be 1,2-, 1,3- or 1,2,4-.: The above defined aromatic compounds can be used both solely and in combination of two kinds or more. Especially preferable aromatic hydrocarbons are the alkylbenzenes with side chains having 1 to 4 carbon atoms in total. More particularly, they are exemplified by toluene, xylene, ethylbenzene, methylethylbenzene, trimethylbenzene, propylbenzene and butylbenzenezene.

In the method of the present invention, the catalyst is quite important in order to attain the reaction of the first step to dimerize and/or codimerize the styrenes selectively and the reaction of the second step to aralkylate the aromatic hydrocarbons without causing the undesirable side reaction of cyclization to occur. The catalyst used in the method of the present invention is at least one fluoroalkyl sulfonic acid which is represented by the general formula: $RCF_2SO_3H$ in which the symbol R is Cl, F or $C_nF_pCl_{2n+1-p}$ wherein n is an integer from 1 to 3 and p is also an integer from 1 to $2n+1$. The above defined compounds are very strong as acids, that is, the acid strengths of them exceed the strength of 100% sulfuric acid, therefore, they belong to the so-called "super acids". (cf. G. A. Olah, "Friedel-Crafts Chemistry", John Wiley & Sons, p. 367 (1973)). As the above defined catalysts, when difluorochloromethane sulfonic acid (R=Cl), trifluoromethane sulfonic acid (R=F), pentafluoroethane sulfonic acid ($R=CF_3$), perfluoropropane sulfonic acid ($R=C_2F_5$) and perfluorobutane sulfonic acid ($R=C_3F_7$) are used, the ratio of conversion from styrenes into distyrenated aromatic compounds can be much improved and quite desirable results can be obtained.

The desirable quantity of the catalyst used in the reaction is 0.2 millimole or more per 1 mole of styrenes. Even though the ratio of conversion from styrenes into unsaturated dimers and/or codimers is not raised with the increase of the concentration of the catalyst, the quantity of 1.0 millimole or more of the catalyst is practically desirable in order to reduce the reaction time until the reaction is finished.

The reaction temperature can be properly selected in the range of $-5°$ C. to 150° C., however, it may desirably be in the range of 10° C. to 110° C. When the reaction temperature is lower than $-5°$ C., trimers and other heavier polymers and/or copolymers and further resin like high polymers are formed in the first step reaction and the reaction rate becomes low in the aralkylation of the second step reaction. Therefore, it is not desirable. On the other hand, when the reaction temperature exceeds 150° C., the thermal polymerization of the raw material styrenes and the products of unsaturated dimers and/or codimers are caused to occur in the first step reaction of the unsaturated dimerization and/or codimerization. Therefore, such a high temperature is not desirable since the ratio of conversion into the objective material is lowered. Further, when the second step reaction of aralkylation is carried out at a temperature above 150° C., the elimination and isomerization of the side chain alkyl groups of the other reaction materials, that is, the aromatic hydrocarbons, are disadvantageously caused to occur.

In the method of the present invention, the pressure of reaction is not an essential factor and, if the reaction materials and reaction solvents are in liquid state, the value of reaction pressure does not exert any influence to the ratio of conversion into the aimed products. The pressure of reaction may well be changed in accordance with the boiling points of raw materials and the reaction temperature, in order to maintain the reaction system in a liquid state. While, the pressure of 30 $Kg/cm^2$ or less is generally desirable.

In the first step reaction of the present invention, the viscosity of reaction mixture rises with the progress of the reaction, therefore, the use of a solvent is desirable so as to control the viscosity. It is necessary that the solvent for controlling the viscosity is of inactive to the reaction. For instance, the compounds having carbonyl groups such as ketone, carboxylic acid, ester and aldehyde, the compounds having a functional group containing a nitrogen atom, oxygen atom or sulfur atom such as amine, alcohol and thiophene, and aromatic compounds cannot be used as the solvents. Exemplified as the desirable solvents are paraffins, isoparaffins and cycloparaffins and their halides. Even though the boiling points of these viscosity controlling solvents are not the essential factors in the method of the present invention, when a solvent containing a component having an excessively high boiling point is used, there is a possibility that some problem arises in the solvent recovering process. In other words, the used solvent remains in the aimed product of polycyclic aromatic hydrocarbons. However, when the remaining solvent does not cause any problem in the use of the polycyclic aromatic hydrocarbons, the above-mentioned inert solvents can be used without any restriction. In view of the easiness in the solvent recovery and the effect to reduce viscosity, the boiling points of the solvents are preferably in the range of 50° C. to 160° C., while this factor does not restrict the method of the present invention. The solvent used in the first step reaction can be used as a part of the solvent for the second step reaction without being separated from the unsaturated dimer and/or codimer and the catalyst, however, when the separation of the solvent is easy, the second step reaction may also be carried out after the removal of solvent.

In the following, the manner of practical working of the method of the present invention will be described in more detail.

In order to avoid the undesirable reaction of saturated dimerization and/or codimerization and the conversion into heavier materials of higher molecular weights, it is important to select the concentration of styrene as one of the reaction materials as well as the selection of the quantity of catalyst and the level of reaction temperature. The concentration of styrenes used for the reaction is desirably in the range of 0.01 to 10 moles per one liter of the solvent. When the quantity of the styrenes is large, the temperature rise that is caused by the heat of reaction becomes vigorous and it is liable to occur that the temperature of the reaction system exceeds the above temperature range. In such that case, it is necessary to regulate the reaction temperature by external cooling or by dividing the feed of styrenes into several parts. Under the above reaction conditions, the ratio of reaction generally becomes up to 97% within 120 minutes after the final feeding of the styrenes. The completion of reaction can easily be confirmed by determining the remaining quantity of styrenes periodically after the final feeding of the styrenes.

In the case that the raw material styrenes are styrene, α-methylstyrene, β-methylstyrene and vinyltoluene, the unsaturated dimer of the aimed products in the first step reaction are 1,3-diphenylbutene-1; 2,4-diphenyl-4-methylpentene-2; 1,3-diphenyl-2-methylpentene-1 and 1,3-ditolylbutene-1, respectively. Further, the obtained codimers are the mixture of unsaturated dimers and codimers in accordance with the mixture of the used styrenes. Exemplified as the unsaturated codimers are 2,4-diphenylpentene-2; 1,3-diphenyl-2-methylbutene-1; 1-tolyl-3-phenylbutene-1; 1,3-diphenyl-3-methylbutene-1; 1,3-diphenyl-2,3-dimethylbutene-1; 1-tolyl-3-phenyl-3-methylbutene-1; 1,3-diphenylpentene-1; 2,4-diphenylhexene-2; 1-tolyl-3-phenylpentene-1; 1-phenyl-3-tolyl-butene-1; 2-phenyl-4-tolylpentene-2 and 1,3-ditolylbutene-1. While, the undesirable products of saturated codimers are intramolecular cyclic compounds which are indane derivatives. When styrene is used, the undesirable codimer is 3-phenyl-1-methylindane.

The second step reaction is initiated after the substantial completion of the dimerization of styrenes in the first step reaction, by adding an aromatic hydrocarbon of hydrocarbons to the reaction system. The second step of the reaction may be carried out in the same reaction vessel as that of the first step reaction or in a different reaction vessel. When the second step reaction is performed in a different reaction vessel, a solvent removal process can be placed between the first step and the second step. The object of this second step reaction is to perform the aralkylation of the aromatic hydrocarbon with the unsaturated dimer and/or codimer which are obtained in the first step reaction. The undesirable side reaction in this second step reaction is that the above unsaturated dimer and/or codimer are polymerized or cyclized into saturated dimer and/or codimer of indane derivatives. In accordance with the methods of the present invention, it is possible to suppress these side reactions and to convert selectively into polycyclic aromatic hydrocarbons. The reaction conditions such as the kind and concentration of catalyst, the temperature of reaction and the kind of solvent can be made all the same as those of the first step reaction. The quantity of the aromatic hydrocarbon that is used for the reaction can be freely selected in the range of 0.5 mole or more per 1 mole of styrenes, however, the quantity may preferably be in the rnage of 0.5 to 10 moles per 1 mole of styrenes. Since the aromatic hydrocarbon is excessively used relative to the unsaturated dimer and/or codimer, a part of the aromatic hydrocarbon serves as the reaction solvent. Accordingly, whether the solvent that is used in the first step reaction is further added in the second step reaction or whether more than stoichiometric quantity of one of the reaction materials is employed as the solvent, may be selected in compliance with the type of the second step reaction to be performed.

The method of the present invention is carried out by two steps of reactions as described above, in which the reaction conditions, the kind and use conditions of catalyst are all the same. Therefore, the method of the present invention is quite advantageous in view of the ratio of conversion and the selectivity from the raw materials to the objective products.

The method of the present invention will be further described in detail with reference to several examples and comparative examples.

EXAMPLE 1

A catalyst of 0.3 g of $CF_3SO_3H$ was dissolved into 1 liter of cyclohexane as a solvent and it was stirred at a temperature of 60° C. 500 g of styrene was then added to the above solution, where the temperature rise by the heat of reaction was suppressed by cooling. After the addition of the styrene, the reaction temperature was maintained at 50° C. and the reaction mixture was stirred for further 120 minutes, thereby finishing the first step reaction. The results of gas chromatographic analysis on the reaction product were residual styrene: 0.0 wt. %, unsaturated dimer: 94.5 wt %, saturated dimer: 2.3 wt % and trimer and higher polymers: 3.2 wt %.

Then, 1000 g of o-xylene was added to the above reaction product and the stirring was continued for 120 minutes at 50° C. to finish the second step reaction. After the reaction, the reaction product was neutralized by washing with 5% aqueous solution of sodium hydroxide and water. After recovering 770 g of the solvent of cyclohexane and 775 g of unchanged o-xylene by distillation at the ordinary pressure, reduced pressure distillation was performed at 3 mmHg. The products obtained in the latter distillation were 26 g of a fraction at distilling temperatures of 140°–155° C., 655 g of a fraction at distilling temperatures of 195°–225° C. and 37 g of the bottom residue of polymers. The lighter fraction in the reduced pressure distillation was 3-phenyl-1-methylindane (saturated dimer of styrene) and the heavier fraction was 1-o-xylyl-1,3-diphenylbutane which was a distyrenated-o-xylene.

The ratios of conversion of the styrene used for the reaction, to the saturated dimer and the aimed distyrenated-o-xylene were 5 mole % and 87 mole %, respectively. Therefore, it was understood that the selectivity was good.

EXAMPLES 2 to 5

Several reactions were carried out in like manner as the foregoing Example 1 by using $CF_2ClSO_3H$, $C_2F_5SO_3H$, $C_3F_7SO_3H$ and $C_4F_9SO_3H$ as catalysts and n-octane, trichloroethane, isooctane and carbon tetrachloride as reaction solvents, respectively in Examples of 2 to 5. Shown in the following Table 1 are the reaction conditions such as quantities of catalysts, reaction temperatures, quantities of used styrene and o-xylene and so forth.

TABLE 1

| Example | 2 | 3 | 4 | 5 |
|---|---|---|---|---|
| Reaction Conditions | | | | |
| Catalyst | $CF_2ClSO_3H$ | $C_2F_5SO_3H$ | $C_3F_7SO_3H$ | $C_4F_9SO_3H$ |
| Qty. of catalyst (g) | 5.4 | 16.0 | 9.6 | 1.3 |
| Solvent | Carbon tetrachloride | Isooctane | Trichloroethane | n-Octane |

TABLE 1-continued

| Example | 2 | 3 | 4 | 5 |
|---|---|---|---|---|
| Qty. of solvent (lit.) | 1 | 1 | 1 | 1 |
| Qty. of styrene (g) | 600 | 950 | 450 | 100 |
| Qty. of o-xylene (g) | 950 | 3500 | 1100 | 250 |
| Reaction temp. (°C.) | 30 | 80 | 90 | 20 |
| First Step Reaction | | | | |
| Residual styrene (wt %) | 0.0 | 0.0 | 0.0 | 0.0 |
| Unsaturated dimer (wt %) | 91.6 | 88.4 | 93.7 | 95.1 |
| Saturated dimer (wt %) | 3.3 | 4.6 | 3.6 | 2.1 |
| Polymers (wt %) | 5.1 | 7.0 | 2.7 | 2.8 |
| Second Step Reaction | | | | |
| Styrene dimer (g) | 48 | 102 | 41 | 8 |
| Distyrenated-o-xylene (g) | 785 | 1268 | 596 | 135 |
| Selectivity (mole %) *[2] | 87 | 88 | 88 | 89 |

Notes:
*[1] The sum of saturated and unsaturated ones.
*[2] The selectivity of distyrenated product against the raw material styrene. The same shall apply in TABLE 2.

EXAMPLES 6 to 9

These Examples were carried out in like manner as the forgoing Example 1, wherein $CF_3SO_3H$ was used as a catalyst, trichloroethane as a reaction solvent, α-methylstyrnee and vinyltoluene (weight ratio of m-:p- =65:35) as styrenes, and diethyl biphenyl, toluene, monoisopropyl naphthalene and pseudocumene as aromatic hydrocarbons. The reaction conditions such as quantities of catalyst, reaction temperatures, the kinds and quantities of styrenes, and the kinds and quantities of aromatic hydrocarbons are shown in the following Table 2.

TABLE 2

| Example | 6 | 7 | 8 | 9 |
|---|---|---|---|---|
| Reaction Conditions | | | | |
| Qty. of catalyst (g) | 1 | 1 | 0.5 | 0.5 |
| Qty. of solvent (lit.) | 1 | 1 | 1 | 1 |
| Reaction temp. (°C.) | 50 | 50 | 50 | 50 |
| Styrenes | α-Methylstyrene | Vinyltoluene | α-Methylstyrene | Vinyltoluene |
| Wty. of above (g) | 550 | 500 | 550 | 500 |
| Aromatic hydrocarbons | Diethyl biphenyl | Toluene | Monoisopropyl naphthalene | Pseudocumene |
| Qty. of above (g) | 1900 | 780 | 1600 | 1020 |
| First Step Reaction | | | | |
| Residual styrene (wt %) | 0.0 | 0.0 | 0.0 | 0.0 |
| Unsaturated dimer (wt %) | 94.0 | 86.1 | 93.8 | 88.6 |
| Saturated dimer (wt %) | 3.7 | 4.7 | 2.8 | 5.1 |
| Polymers | 2.3 | 9.2 | 3.4 | 6.3 |
| Second Step Reaction | | | | |
| Styrene dimer (g) | 62 | 50 | 36 | 55 |
| Distyrenated aromatic hydrocarbon (g) | 900 | 562 | 850 | 620 |
| Selectivity (mole %) | 86 | 81 | 90 | 82 |

COMPARATIVE EXAMPLE 1

To 1 liter of cyclohexane as a solvent, 1 g of 98% sulfuric acid as a catalyst was added and the mixture was stirred at 70° C. Then, 500 g of styrene was added to the above mixture, in which the temperature rise by the heat of reaction was suppressed by cooling. After the addition of the styrene, the reaction temperature was maintained at 50° C. and the reaction mixture was stirred for further 120 minutes. As the result, much gel-like polymer was formed. According to gas chromatographic analysis on the reaction product, even though the residual styrene was 0.0%, the unsaturated dimer that was aimed in the first step reaction was 1.7% and the saturated dimer was 4.3%.

Therefore, without the necessity to try the second step reaction, it was understood that the object of the present invention could not be attained.

COMPARATIVE EXAMPLE 2

To 1 liter of n-octane as a solvent, 50 g of activated clay as a catalyst was added and the mixture was stirred at 90° C. Then, 50 g of styrene was added to the above mixture, in which the temperature rise by the heat of reaction was suppressed by cooling. After the addition of the styrene, the reaction mixture was stirred for further 120 minutes with maintaining the temperature at 90° C. The results of gas chromatographic analysis on the reaction product were the residual styrene: 23.6%, saturated dimer: 57.3%, unsaturated dimer: 6.7% and polymerization products: 12.4%.

Therefore, without the necessity to try the second step reaction, it was understood that the object of the present invention could not be attained.

Although the present invention has been described in connection with preferred examples thereof, many variations and modifications will now become apparent to those skilled in the art. It is preferred, therefore, that the present invention be limited not by the specific disclosure herein but only by the appended claims.

What is claimed is:

1. A method for preparing polycyclic aromatic hydrocarbons in which at least one member selected from the group consisting of styrene, α-methylstyrene, β- methylstyrene and vinyltoluene is dimerized and/or codimerized to produce unsaturated dimer and/or codimer in the first step reaction and said unsaturated dimer and/or codimer is caused to react with an aromatic hydrocarbon or hydrocarbons in the second step reaction and both said first and second step reactions are carried out in the presence of a catalyst which is represented by the general formula: $RCF_2SO_3H$, in which the symbol R is Cl, F or $C_nF_pCl_{2n+1-p}$, wherein n is an integer from 1 to 3, inclusive, and p is also an integer from 1 to 2n+1, inclusive.

2. The method for preparing polycyclic aromatic hydrocarbons as claimed in claim 1, wherein said polycyclic aromatic hydrocarbon is an equimolar adduct of said unsaturated dimer and/or codimer and said aromatic hydrocarbon.

3. The method for preparing polycyclic aromatic hydrocarbons as claimed in claim 1, wherein said first and second step reactions are carried out at temperatures in the range of −5° C. to +150° C.

4. The method for preparing polycyclic aromatic hydrocarbons as claimed in claim 1, wherein said catalyst is at least one member selected from the group consisting of difluorochloromethane sulfonic acid, trifluoromethane sulfonic acid, pentafluoroethane sulfonic acid, perfluoropropane sulfonic acid and perfluorobutane sulfonic acid.

5. The method for preparing polycylic aromatic hydrocarbons as claimed in claim 1, wherein said aromatic hydrocarbon is at least one member selected from the group of saturated aromatic hydrocarbons of benzene, alkyl benzenes, tetralines, naphthalenes, biphenyls and diphenyl alkanes.

6. The method for preparing polycyclic aromatic hydrocarbons as claimed in claim 1 or 5, wherein said aromatic hydrocarbon is at least one member selected from the group consisting of toluene, xylene, ethylbenzene, methylethylbenzene, trimethylbenzene, propylbenzene and butylbenzene.

7. The method for preparing polycyclic aromatic hydrocarbons as claimed in claim 1, wherein said first and/or second step reactions are carried out by using a solvent or solvents which are selected from paraffins, isoparaffins, cycloparaffins and their halides.

* * * * *